United States Patent
Ogi et al.

(10) Patent No.: US 12,222,289 B2
(45) Date of Patent: Feb. 11, 2025

(54) REACTION PROCESSOR

(71) Applicant: Go!Foton, Inc., Tsukuba (JP)

(72) Inventors: Shuya Ogi, Tokyo (JP); Takashi Fukuzawa, Tokyo (JP)

(73) Assignee: Go!Foton, Inc., Ibaraki (JP)

(*) Notice: Subject to any disclaimer, the term of this patent is extended or adjusted under 35 U.S.C. 154(b) by 1025 days.

(21) Appl. No.: 17/124,655

(22) Filed: Dec. 17, 2020

(65) Prior Publication Data

US 2021/0102897 A1    Apr. 8, 2021

Related U.S. Application Data

(63) Continuation of application No. PCT/JP2019/025331, filed on Jun. 26, 2019.

(30) Foreign Application Priority Data

Jul. 6, 2018   (JP) .................... 2018-129123

(51) Int. Cl.
   *G01N 21/64* (2006.01)
   *C12Q 1/686* (2018.01)
   *G01N 21/17* (2006.01)

(52) U.S. Cl.
   CPC ......... *G01N 21/6486* (2013.01); *C12Q 1/686* (2013.01); *G01N 2021/174* (2013.01)

(58) Field of Classification Search
   CPC ......... G01N 21/6486; G01N 2021/174; C12Q 1/686

(Continued)

(56) References Cited

U.S. PATENT DOCUMENTS 9,193,996 B2 * 11/2015 Buermann ........... C12Q 1/6874
9,658,222 B2 *  5/2017 Moll ................... G02B 6/0095
(Continued)

FOREIGN PATENT DOCUMENTS

CN    101893571 A    11/2010
CN    202057580 U    11/2011
(Continued)

OTHER PUBLICATIONS

Office Action issued Sep. 13, 2022 in Indian Application No. 202017054515.
(Continued)

*Primary Examiner* — Jonathan M Hurst
(74) *Attorney, Agent, or Firm* — Sughrue Mion, PLLC

(57) ABSTRACT

A reaction processor includes: a reaction processing vessel; a first optical head including a first objective lens OB1 for irradiating a sample with first excitation light and collecting first fluorescence generated from the sample; a second optical head including a second objective lens for irradiating a sample with second excitation light and collecting second fluorescence generated from the sample; and a holding member holding the first optical head and the second optical head. The wavelength range of the first fluorescence and the wavelength range of the second excitation light at least partially overlap with each other. A distance between the optical axis of the first objective lens and the optical axis of the second objective lens satisfies $2 \cdot P_0 + 2 \cdot P_1 + 4 \cdot P_2 + 4 \cdot P_3 < P$, $P_0 = L \cdot NA/\sqrt{(1-NA^2)}$, $P_1 = t_1 \cdot NA/\sqrt{(n_1^2 - NA^2)}$, $P_2 = t_2 \cdot NA/\sqrt{(1-NA^2)}$, and $P_3 = t_3 \cdot NA/\sqrt{(n_3^2 - NA^2)}$.

4 Claims, 7 Drawing Sheets

(58) Field of Classification Search
USPC ...................................................... 435/288.7
See application file for complete search history.

(56) References Cited

U.S. PATENT DOCUMENTS

| | | | |
|---|---|---|---|
| 2008/0053829 A1* | 3/2008 | Hayashida | G01N 21/6428 |
| | | | 204/600 |
| 2008/0297792 A1 | 12/2008 | Kim et al. | |
| 2011/0256532 A1 | 10/2011 | Sano et al. | |
| 2015/0024401 A1* | 1/2015 | Sano | C12Q 1/68 |
| | | | 435/6.12 |

FOREIGN PATENT DOCUMENTS

| | | |
|---|---|---|
| JP | 2005-091242 A | 4/2005 |
| JP | 2007-71608 A | 3/2007 |
| JP | 2007-285999 A | 11/2007 |
| JP | 2007-300896 A | 11/2007 |
| JP | 2008-157814 A | 7/2008 |
| JP | 2009-232700 A | 10/2009 |
| JP | 2011-027748 A | 2/2011 |
| JP | 2013-524169 A | 6/2013 |
| JP | 2015-514218 A | 5/2015 |
| JP | 2016-095315 A | 5/2016 |
| JP | 2016-165247 A | 9/2016 |
| KR | 10-2015-0127762 A | 11/2015 |
| WO | 2016/157270 A1 | 10/2016 |
| WO | 2017/115863 A1 | 7/2017 |
| WO | 2017/119382 A1 | 7/2017 |
| WO | 2017/145230 A1 | 8/2017 |
| WO | 2017/199933 A1 | 11/2017 |

OTHER PUBLICATIONS

Chinese Office Action dated Dec. 4, 2023 in Application No. 201980044608.5.
International Preliminary Report on Patentability with a Translation of the Written Opinion in International Application No. PCT/JP2019/025331 issued on Jan. 12, 2021.
International Search Report dated Sep. 3, 2019 issued by the International Patent Office in Application No. PCT/JP2019/025331.
Communication dated Aug. 27, 2019 from the Japanese Patent Office in Application No. 2018-129123.
Communication dated Oct. 23, 2019 from the Japanese Patent Office in Application No. 2018-129123.
Extended European Search Report dated Dec. 3, 2021 from the European Patent Office in EP Application No. 19829747.5.
Communication dated Jul. 10, 2024 from the State Intellectual Property Office of the P.R. of China in Application No. 201980044608.5.

* cited by examiner

REACTION PROCESSOR

BACKGROUND OF THE INVENTION

1. Field of the Invention

The present invention relates to a reaction processor used for a polymerase chain reaction (PCR).

BACKGROUND ART

Genetic testing is widely used for examinations in a wide variety of medical fields, identification of farm products and pathogenic microorganisms, safety assessment for food products, and even for examinations for pathogenic viruses and a variety of infectious diseases. In order to detect a minute amount of DNA with high sensitivity, a method for analyzing a product obtained by amplifying a part of DNA is known. Above all, a method using PCR is a remarkable technique for selectively amplifying a certain portion of a very minute amount of DNA collected from an organism or the like.

PCR applies a predetermined thermal cycle to a sample in which a biological sample containing DNA and a PCR reagent containing a primer, an enzyme, and the like are mixed, causes denaturation, annealing, and an elongation reaction repeatedly, and selectively amplifies a specific portion of DNA.

It is a common practice to perform PCR by putting a predetermined amount of a target sample into a PCR tube or a reaction processing vessel such as a microplate (microwell) in which a plurality of holes is formed. However, in recent years, PCR using a reaction processing vessel (also referred to as "chip") including a micro-channel that is formed on a substrate has been put to practical use (e.g. Patent Document 1).

[Patent Document 1] Japanese Patent Application Publication No. 2009-232700

SUMMARY OF THE INVENTION

In PCR using such a reaction processing vessel including a channel as described above, a fluorescence detection device may be used for the purpose of detecting a quantitative change of a sample. A fluorescent dye is added to a sample, and the sample is irradiated with excitation light using a fluorescence detection device during PCR to detect fluorescence emitted from the sample. Since the intensity of fluorescence emitted from the sample increases as amplification of the DNA proceeds, the intensity value of the fluorescence can be used as an index serving as a decision-making factor for progress of PCR or termination of the reaction.

In PCR, some amplification targets often use a reagent in which a plurality of fluorescent dyes is mixed. In this case, a plurality of fluorescence detection devices needs to be disposed. In particular, in a reaction processor for detecting fluorescence from a sample while moving the sample in a channel formed in a plate-like reaction processing vessel, in order to detect fluorescence from the sample that passes through a single channel having, for example, a cross section of 2 mm$^2$ or less, it is necessary to dispose a plurality of fluorescence detection devices in an extension direction of the channel.

For example, when 0-157 is amplified by PCR, VT1 and VT2 are measured simultaneously. For example, a test kit (FIK-362) manufactured by Toyobo Co., Ltd. uses ROX (fluorescent dye that is excited by irradiation with substantially green light and emits substantially red fluorescence, and characteristic of such fluorescence is hereinafter referred to as "green excitation/red fluorescence") and Cy5 (red excitation/infrared fluorescence) as fluorescent dyes. In this case, two fluorescence detection devices are required.

When a norovirus is detected, G1 and G2 are measured simultaneously. For example, both a test kit (RR255A) manufactured by Takara Bio Inc. and a test kit (FIK-253) manufactured by Toyobo Co., Ltd. use FAM (blue excitation/green fluorescence), ROX (green excitation/red fluorescence), and Cy5 (red excitation/infrared fluorescence) as fluorescent dyes. In this case, three fluorescence detection devices are required.

As described above, when fluorescence is detected for a sample that passes through a channel using a plurality of fluorescence detection devices, interference may occur between the fluorescence detection devices. Hereinafter, description will be made based on an example.

When FAM and ROX are simultaneously added to a sample and used as fluorescent dyes, a wavelength range of light corresponding to substantially green of excitation light to be emitted for exciting ROX may partially overlap with a wavelength range of light corresponding to substantially green of fluorescence emitted from FAM. In this case, when a part of the excitation light emitted for exciting ROX enters a photodetector such as a photoelectric conversion element for detecting fluorescence emitted from FAM, the excitation light becomes a noise and may make measurement with high sensitivity impossible. Usually, the light quantity of excitation light is several tens µW, while the light quantity of fluorescence to be detected is on the order of several µW or less. The fluorescence detection device detects such a minute amount of fluorescence. However, if only a part of the excitation light reaches the photodetector, the excitation light appears as a large noise.

When ROX and Cy5 are simultaneously added to a sample and used as fluorescent dyes, a wavelength range of light corresponding to substantially red of excitation light to be emitted for exciting Cy5 may partially overlap with a wavelength range of light corresponding to substantially red of fluorescence emitted from ROX. Also in this case, when a part of the excitation light emitted for exciting Cy5 enters a photodetector for detecting fluorescence emitted from ROX, the excitation light becomes a noise and may make fluorescence measurement with high sensitivity impossible.

The present invention has been achieved in view of such circumstances, and an object thereof is to provide a technique capable of suppressing interference among a plurality of fluorescence detection devices in a reaction processor including the fluorescence detection devices.

Means to Solve the Problem

In order to solve the above problems, a reaction processor according to one embodiment of the present invention includes: a reaction processing vessel including a substrate having a first main surface with a channel through which a sample moves, and a channel sealing film disposed on the first main surface so as to seal the channel; a first optical head including a first objective lens for irradiating a sample in the channel with first excitation light and collecting first fluorescence generated from the sample by irradiation with the first excitation light; a second optical head including a second objective lens for irradiating a sample in the channel with second excitation light and collecting second fluorescence generated from the sample by irradiation with the second excitation light; and a holding member holding the first optical head and the second optical head. The first optical head and the second optical head are disposed side by side in a longitudinal direction of the channel. A wavelength range of the first fluorescence and a wavelength range of the second excitation light at least partially overlap with each other. A distance P between the optical axis of the first objective lens and the optical axis of the second objective lens satisfies $2 \cdot P_0 + 2 \cdot P_1 + 4 \cdot P_2 + 4 \cdot P_3 < P$, in which $P_0 = L \cdot NA/\sqrt{(1-NA^2)}$, $P_1 = t_1 \cdot NA/\sqrt{(n_1^2 - NA^2)}$, $P_2 = t_2 \cdot NA/\sqrt{(1-NA^2)}$, and $P_3 = t_3 \cdot NA/\sqrt{(n_3^2 - NA^2)}$ (in which L represents a distance from the holding member to the channel sealing film, $t_1$ represents the thickness of the channel sealing film, $t_2$ represents the depth of the channel, $t_3$ represents a thickness from a bottom of the channel to the second main surface of the substrate, NA represents the numerical aperture of the first objective lens and the second objective lens, $n_1$ represents the refractive index of the channel sealing film, and $n_3$ represents the refractive index of the substrate).

The distance P may further satisfy $1.1 \times (2 \cdot P_0 + 2 \cdot P_1 + 4 \cdot P_2 + 4 \cdot P_3) \leq P$, more preferably $1.2 \times (2 \cdot P_0 + 2 \cdot P_1 + 4 \cdot P_2 + 4 \cdot P_3) \leq P$.

The distance P may satisfy $P \leq S - 2 \times \Delta S$ (in which S represents the length of a linear portion of the channel in which the first optical head and the second optical head are disposed, and $\Delta S$ represents 1 (mm)).

A light absorbing layer for absorbing excitation light may be disposed between a bottom of the channel in the substrate and the second main surface.

Another embodiment of the present invention also relates to a reaction processor. This reaction processor includes: a reaction processing vessel including a substrate having a first main surface with a channel through which a sample moves, and a channel sealing film disposed on the first main surface so as to seal the channel; a first optical head including a first objective lens for irradiating a sample in the channel with first excitation light and collecting first fluorescence generated from the sample by irradiation with the first excitation light; a second optical head including a second objective lens for irradiating a sample in the channel with second excitation light and collecting second fluorescence generated from the sample by irradiation with the second excitation light; and a holding member holding the first optical head and the second optical head. The first optical head and the second optical head are disposed side by side in a longitudinal direction of the channel. A wavelength range of the first fluorescence and a wavelength range of the second excitation light at least partially overlap with each other. A light absorbing layer for absorbing excitation light is disposed on the substrate.

The light absorbing layer may be formed such that an absorption coefficient α satisfies $\alpha \geq 0.58/t_3'$ (in which $t_3'$ represents the thickness of the light absorbing layer).

The light absorbing layer may be formed such that an absorption coefficient α satisfies $\alpha \geq 0.75/t_3'$ (in which $t_3'$ represents the thickness of the light absorbing layer).

The light absorbing layer may be formed such that an absorption coefficient α satisfies $\alpha \geq 1.15/t_3'$ (in which $t_3'$ represents the thickness of the light absorbing layer).

The light absorbing layer may be disposed between a bottom of the channel and the second main surface of the substrate. The light absorbing layer may be disposed on the second main surface of the substrate.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

Figure 1A:
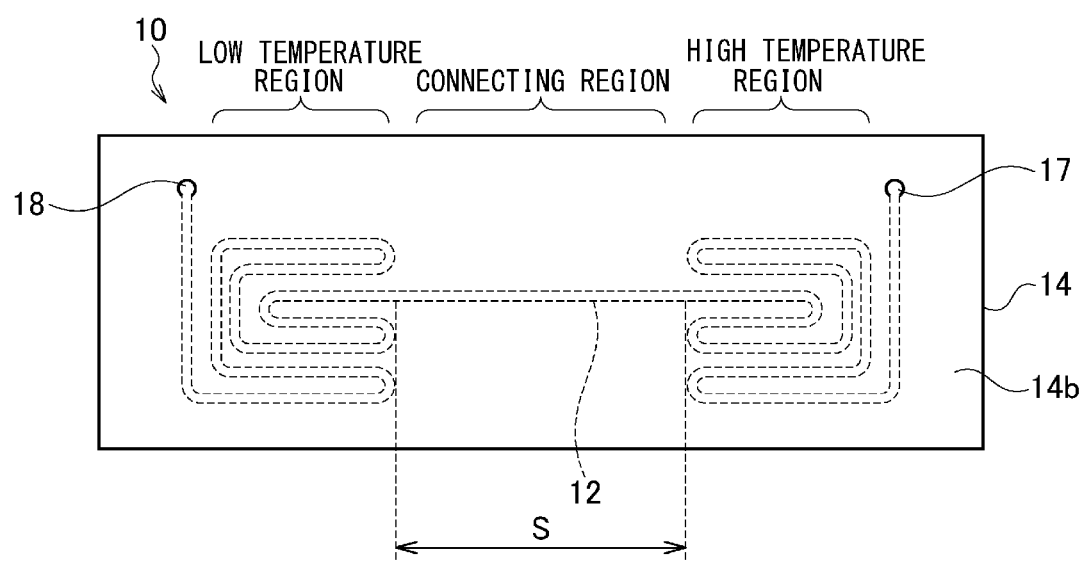
FIGS. 1A and 1B are views for explaining a reaction processing vessel usable in a reaction processor according to an embodiment of the present invention.

Hereinafter, a reaction processor according to an embodiment of the present invention will be described. The same or equivalent constituting elements, members, and processes illustrated in the drawings are denoted by the same reference numerals, and duplicative explanations will be omitted appropriately. The embodiment does not limit the invention and is described for illustrative purposes, and all the features described in the embodiment and a combination thereof are not necessarily essential to the invention.

Figure 1B:
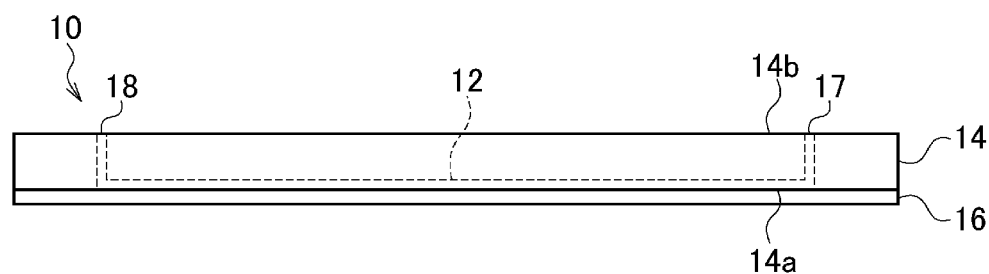

FIGS. 1A and 1B are views for explaining a reaction processing vessel 10 usable in a reaction processor according to an embodiment of the present invention. FIG. 1A is a plan view of the reaction processing vessel 10, and FIG. 1B is a front view of the reaction processing vessel 10.

As illustrated in FIGS. 1A and 1B, the reaction processing vessel 10 includes a substrate 14 and a channel sealing film 16.

The substrate 14 is preferably formed of a material that is stable under temperature changes and is resistant to a sample solution to be used. Furthermore, the substrate 14 is preferably formed of a material having good moldability, a good transparency and barrier property, and a low self-fluorescence property. As such a material, an inorganic material such as glass or silicon (Si) and a resin such as acrylic polymer, polypropylene, polyester, or silicone are preferable. Above all, cycloolefin polymer is preferable. For example, the dimensions of the substrate 14 are a long side of 75 mm, a short side of 25 mm, and a thickness of 4 mm.

A groove-like channel 12 is formed on a first main surface 14a of the substrate 14, and this channel 12 is sealed by the channel sealing film 16. For example, the dimensions of the channel 12 formed on the first main surface 14a of the substrate 14 are a width of 0.7 mm and a depth of 0.7 mm. A first communication port 17 communicating with the outside is formed at one end of the channel 12 in the substrate 14. A second communication port 18 is formed at the other end of the channel 12 in the substrate 14. The pair of first communication port 17 and second communication port 18 formed at both ends of the channel 12 is formed so as to be exposed to a second main surface 14b (surface opposite to the first main surface 14a) of the substrate 14. Such a substrate can be manufactured by injection molding or cutting with an NC processing machine or the like.

As illustrated in FIG. 1B, the channel sealing film 16 is stuck onto the first main surface 14a of the substrate 14. In the reaction processing vessel 10 according to the embodiment, most of the channel 12 is formed in a groove shape exposed to the first main surface 14a of the substrate 14. This is for making easy molding possible by injection molding using a die or the like. In order to seal this groove and use the groove as a channel, the channel sealing film 16 is stuck onto the first main surface 14a of the substrate 14.

The channel sealing film 16 may have one main surface having adhesiveness or stickiness or may have one main surface including a functional layer that exhibits adhesiveness or stickiness through pressing, irradiation with energy such as an ultraviolet ray, heating, or the like. The channel sealing film 16 has a function of being easily able to be integral with the first main surface 14a of the substrate 14 while being in close contact with the first main surface 14a. The channel sealing film 16 is desirably formed of a material having a low self-fluorescence property, including the part of the layer that exerts the function of adhesion and stickiness. In this respect, a transparent film formed of a resin such as cycloolefin polymer, polyester, polypropylene, polyethylene, or acrylic polymer is suitable, but is not limited thereto. The channel sealing film 16 may be formed of a plate-like glass or plastics. Since rigidity can be expected in this case, the channel sealing film 16 is useful for preventing warpage and deformation of the reaction processing vessel 10.

The channel 12 has a reaction region where temperatures of a plurality of levels can be controlled by a reaction processor described later. By moving a sample such that the sample continuously reciprocates in the reaction region where the temperatures of a plurality of levels are maintained, a thermal cycle can be applied to the sample.

The reaction region of the channel 12 illustrated in FIGS. 1A and 1B includes a meandering channel in which a turn is continuously made by combining a curved portion and a linear portion. When the reaction processing vessel 10 is mounted on a reaction processor described later, the right side of the channel 12 in the drawings is expected to become a relatively high temperature (about 95° C.) region (hereinafter referred to as "high temperature region"), and the left side of the channel 12 is expected to become a lower temperature (about 60° C.) region (hereinafter referred to as "low temperature region"). The reaction region of the channel 12 includes a connecting region connecting the high temperature region to the low temperature region therebetween. The connecting region may be a linear channel.

When the high temperature region and the low temperature region are formed of a meandering channel as in the present embodiment, an effective area of a heater or the like constituting a temperature control means described later can be effectively used, temperature variance in the reaction region is easily reduced, the substantial size of the reaction processing vessel can be reduced, and the size of the reaction processor can be reduced advantageously.

A sample to which a thermal cycle is applied is introduced into the channel 12 from either the first communication port 17 or the second communication port 18. The introduction method is not limited thereto. Alternatively, for example, an appropriate amount of a sample may be directly introduced from the communication port using a pipette, a dropper, a syringe, or the like. Alternatively, an introduction method that is performed while preventing contamination via a cone-shaped needle chip having a filter made of porous PTFE or polyethylene incorporated therein may be used. In general, many types of such needle chips are sold and easily available, and can be used while being attached to a tip of a pipette, a dropper, a syringe, or the like. Furthermore, a sample may be moved to a predetermined position in the channel by discharging and introducing the sample by a pipette, a dropper, a syringe, or the like and then further pushing the sample through pressurization.

Examples of the sample include those obtained by adding a fluorescent dye, a thermostable enzyme, and four types of deoxyribonucleoside triphosphates (dATP, dCTP, dGTP, and dTTP) as PCR reagents to a mixture containing one or more types of DNA. Furthermore, a primer that specifically reacts with DNA to be subjected to a reaction process, and optionally, a fluorescent probe such as TaqMan is further mixed (TaqMan is a registered trademark of Roche Diagnostics Gesellschaft Mit Beschrankter Haftung). A commercially available real-time PCR reagent kit and the like can also be used.

Figure 2:
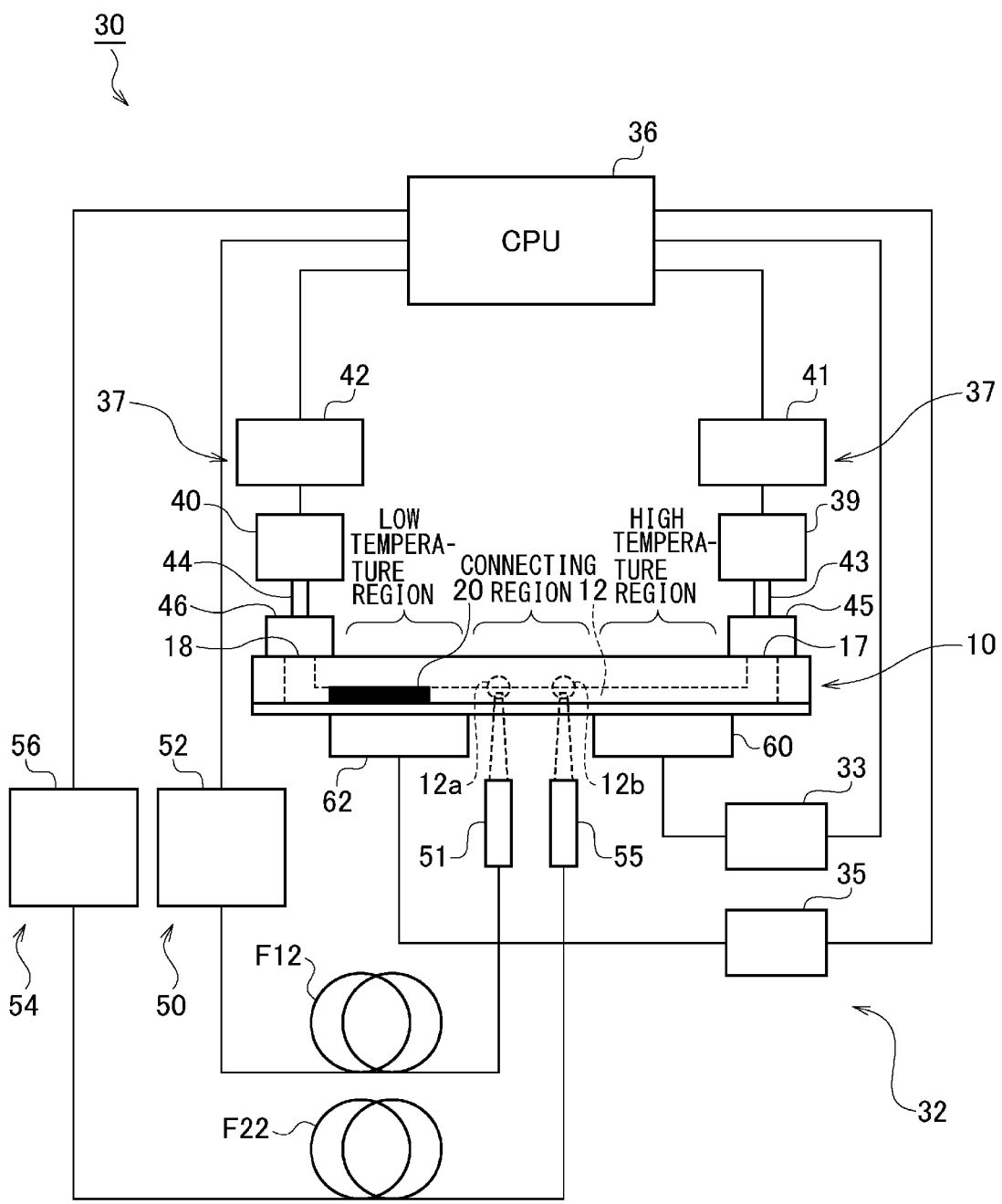
FIG. 2 is a schematic diagram for explaining a reaction processor according to an embodiment of the present invention.

FIG. 2 is a schematic diagram for explaining a reaction processor 30 according to an embodiment of the present invention.

The reaction processor 30 according to the present embodiment includes a reaction processing vessel placing unit (not illustrated) on which the reaction processing vessel 10 is placed, a temperature control system 32, and a CPU 36. As illustrated in FIG. 2, relative to the reaction processing vessel 10 placed on the reaction processing vessel placing unit, the temperature control system 32 can accurately maintain and control the temperature of the right side region of the channel 12 of the reaction processing vessel 10 in the drawing to be about 95° C. (high temperature region) and the temperature of the left side region thereof in the drawing to be about 60° C. (low temperature region).

The temperature control system 32 is for maintaining the temperature of each temperature region of the reaction region and specifically includes a high temperature heater 60 for heating the high temperature region of the channel 12, a low temperature heater 62 for heating the low temperature region of the channel 12, a temperature sensor (not illustrated) for measuring the actual temperature of each temperature region, such as a thermocouple, a high temperature heater driver 33 for controlling the temperature of the high temperature heater 60, and a low temperature heater driver 35 for controlling the temperature of the low temperature heater 62. Information on the actual temperature measured by the temperature sensor is sent to the CPU 36. Based on the information on the actual temperature of each temperature region, the CPU 36 controls each heater driver such that the temperature of each heater is a predetermined temperature. Each heater may be, for example, a resistance heating element or a Peltier element. The temperature control system 32 may further includes another component for improving temperature controllability of each temperature region.

The reaction processor 30 according to the present embodiment further includes a liquid feeding system 37 for moving the sample 20 introduced into the channel 12 of the reaction processing vessel 10 in the channel 12. The liquid feeding system 37 includes a first pump 39, a second pump 40, a first pump driver 41 for driving the first pump 39, a second pump driver 42 for driving the second pump 40, a first tube 43, and a second tube 44.

One end of the first tube 43 is connected to the first communication port 17 of the reaction processing vessel 10. A packing 45 or a seal for securing airtightness is preferably disposed at a connecting portion of the first communication port 17 and one end of the first tube 43. The other end of the first tube 43 is connected to output of the first pump 39. Similarly, one end of the second tube 44 is connected to the second communication port 18 of the reaction processing vessel 10. A packing 46 or a seal for securing airtightness is preferably disposed at a connecting portion of the second communication port 18 and one end of the second tube 44. The other end of the second tube 44 is connected to output of the second pump 40.

Each of the first pump 39 and the second pump 40 may be, for example, a micro blower pump including a diaphragm pump. As each of the first pump 39 and the second pump 40, for example, a micro blower pump (MZB1001 T02 model) manufactured by Murata Manufacturing Co., Ltd. can be used. While this micro blower pump can increase the pressure on a secondary side to be higher than that on a primary side during operation, the pressure on the primary side and the pressure on the secondary side become equal at the moment when the pumps are stopped or when the pumps are stopped.

The CPU 36 controls air supply and pressurization from the first pump 39 and the second pump 40 via the first pump driver 41 and the second pump driver 42. The air supply and pressurization from the first pump 39 and the second pump 40 act on the sample 20 in the channel 12 through the first communication port 17 and the second communication port 18 and become a propulsive force to move the sample 20. More specifically, by alternately operating the first pump 39 and the second pump 40, the pressure applied to either end surface of the sample 20 becomes larger than the pressure applied to the other end, and a propulsive force related to the movement of the sample 20 can thus be obtained. By alternately operating the first pump 39 and the second pump 40, the sample 20 can be moved in a reciprocating manner in the channel 12 and can be stopped in each temperature region of the channel 12 of the reaction processing vessel 10. As a result, a thermal cycle can be applied to the sample 20. More specifically, by repeatedly applying a step of denaturation in the high temperature region and a step of annealing and elongation in the low temperature region, target DNA in the sample 20 is selectively amplified. In other words, the high temperature region can be regarded as a denaturation temperature region, and the low temperature region can be regarded as an annealing and elongation temperature region. Residence time in each temperature region can be appropriately set by changing time during which the sample 20 stops at a predetermined position in each temperature region.

The reaction processor 30 according to the present embodiment further includes a first fluorescence detection device 50 and a second fluorescence detection device 54. As described above, the sample 20 contains a predetermined fluorescent dye. Since the intensity of a fluorescence signal emitted from the sample 20 increases as the amplification of DNA proceeds, fluctuation of the intensity value of the fluorescence signal can be used as an index serving as a decision-making factor for progress of PCR or termination of the reaction.

As the first fluorescence detection device 50 and the second fluorescence detection device 54, an optical fiber-type fluorescence detection device FLE-510 manufactured by Nippon Sheet Glass Co., Ltd., which is a very compact optical system that can perform measurement rapidly and can detect fluorescence regardless of whether a place is a bright place or a dark place, can be used. This optical fiber-type fluorescence detection device can be tuned such that wavelength characteristics of excitation light/fluorescence thereof are suitable for characteristics of fluorescence emitted from the sample 20 and can provide an optimum optical and detection system for each of samples having various characteristics. Furthermore, the optical fiber-type fluorescence detector is suitable for detecting fluorescence from a sample present in a small or narrow region such as a channel because of the small diameter of a light beam brought by the optical fiber-type fluorescence detection device.

The first fluorescence detection device 50 includes a first optical head 51, a first fluorescence detection excitation light source/detector module 52, and an optical fiber F12 connecting the first optical head 51 to the first fluorescence detection excitation light source/detector module 52. Similarly, the second fluorescence detection device 54 includes a second optical head 55, second fluorescence detection excitation light source/detector module 56, and an optical fiber F22 connecting the second optical head 55 to second fluorescence detection excitation light source/detector module 56.

Each of the first fluorescence detection excitation light source/detector module 52 and the second fluorescence detection excitation light source/detector module 56 includes a light source for excitation light, a wavelength multiplexer/demultiplexer, a fluorescence detector, a driver for controlling these, and the like. Each of the first optical head 51 and the second optical head 55 is formed of an optical system such as a lens and has a function of directionally irradiating a sample with excitation light and collecting fluorescence emitted from the sample. Fluorescence collected by the first optical head 51 and the second optical head 55 is separated from excitation light by the wavelength multiplexer/demultiplexers in the first fluorescence detection excitation light source/detector module 52 and the second fluorescence detection excitation light source/detector module 56 through the optical fibers F12 and F22, respectively, and converted into electrical signals by the fluorescence detectors. Details of the configuration of the fluorescence detection device will be described later.

In the reaction processor 30 according to the present embodiment, the first optical head 51 is disposed such that fluorescence can be detected from the sample 20 passing through a partial region 12a (referred to as "first fluorescence detection region 12a") in the connecting region connecting the high temperature region to the low temperature region. The second optical head 55 is disposed such that fluorescence can be detected from the sample 20 passing through another partial region 12b (referred to as "second fluorescence detection region 12b") in the connecting region. The reaction progresses by reciprocating the sample 20 repeatedly in the channel 12, and predetermined DNA contained in the sample 20 is amplified. Therefore, by monitoring a change in the amount of detected fluorescence, the degree of progress of DNA amplification can be found in real time.

Figure 3:
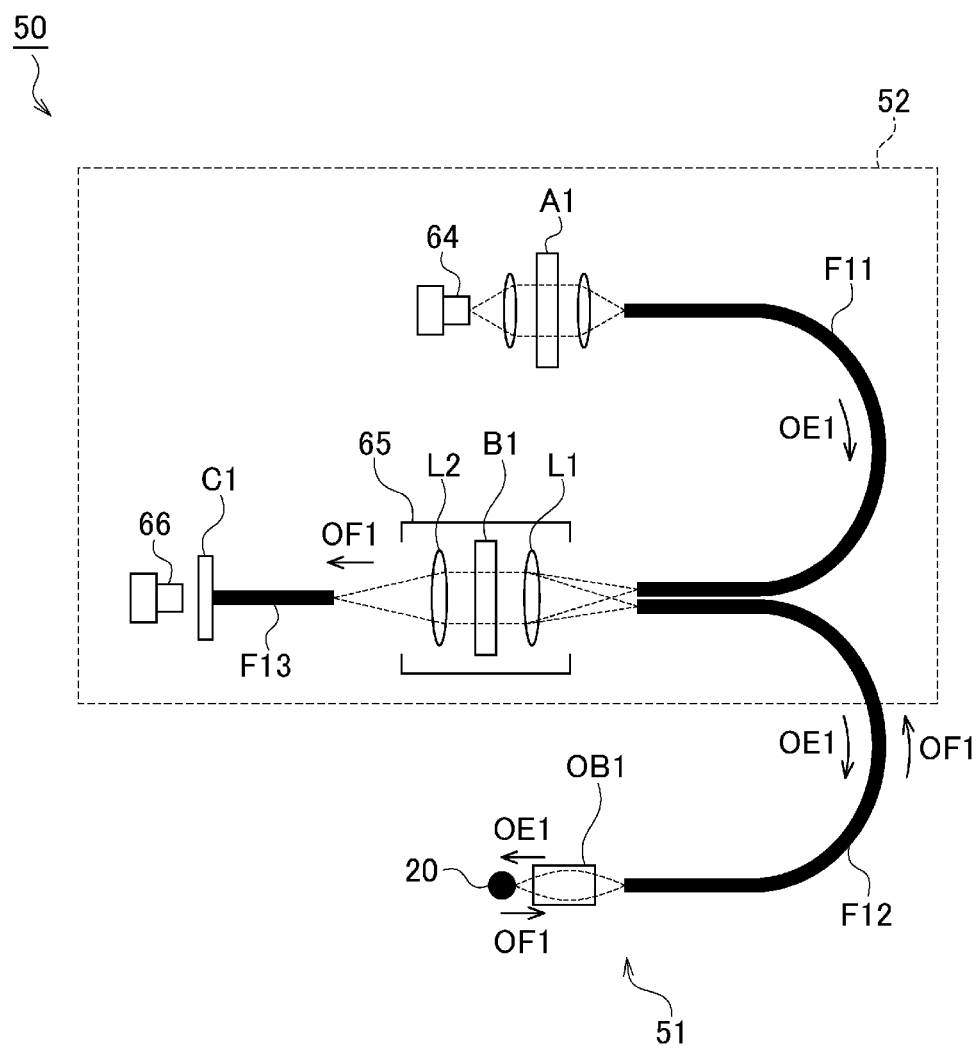
FIG. 3 is a diagram for explaining the configuration of a fluorescence detection device.

FIG. 3 is a diagram for explaining the configuration of a fluorescence detection device. FIG. 3 illustrates the configuration of the first fluorescence detection device 50. However, the second fluorescence detection device 54 also has the same configuration except that the central wavelength of a band pass filter is different.

As illustrated in FIG. 3, the first fluorescence detection device 50 includes the first optical head 51, the first fluorescence detection excitation light source/detector module 52, and the optical fiber F12 connecting the first optical head 51 to the first fluorescence detection excitation light source/detector module 52. The first fluorescence detection excitation light source/detector module 52 includes a first excitation light source 64, a first wavelength multiplexer/demultiplexer 65, and a first fluorescence detector 66, and these functional elements are connected by optical fibers. Excitation light and fluorescence are propagated in the optical fibers.

A band pass filter A1 is disposed around the first excitation light source 64 so as to transmit excitation light emitted from the first excitation light source 64. The first wavelength multiplexer/demultiplexer 65 includes a band pass filter B1. A band pass filter Cl is disposed around the first fluorescence detector 66 so as to transmit fluorescence entering the first fluorescence detector 66. The wavelength characteristics of these band pass filters are designed, for example, according to wavelength characteristics related to excitation/fluorescence of a fluorescent dye such as FAM. Each of the band pass filters has a spectral function of transmitting light in a specific wavelength range with high efficiency (for example, a transmittance of 75% or more) and reflects light outside the wavelength range with high efficiency (for example, a reflectance of 75% or more, desirably, 85% or more).

In the present embodiment, the first fluorescence detection device 50 can detect fluorescence from a sample containing FAM as a fluorescent dye.

The first excitation light source 64 is not particularly limited as long as being able to disperse light having a target wavelength later, and, for example, LD, LED, or a white light source can be used. Excitation light emitted from the first excitation light source 64 is dispersed by the band pass filter A1, and only light having a wavelength in a predetermined range with a central wavelength of about 470 nm (hereinafter referred to as "excitation light OE1") is propagated in an optical fiber F11.

The excitation light OE1 enters the first wavelength multiplexer/demultiplexer 65, is collimated by a lens L1, and then reaches the band pass filter B1. Since the band pass filter B1 is designed so as to reflect the excitation light OE1, the excitation light OE1 is collected again by the lens L1 and enters the optical fiber F12. The excitation light OE1 is propagated in the optical fiber F12 and reaches the first optical head 51. The first optical head 51 includes a first objective lens OB1, and the sample 20 is irradiated with the excitation light OE1 as excitation light at a predetermined working distance. FIG. 3 illustrates an example in which a graded refractive index type lens is used as the first objective lens OB1.

When the sample 20 is irradiated with the excitation light OE1, a fluorescent dye in the sample 20 is excited, and fluorescence OF1 is emitted from the sample 20. The fluorescence OF1 is collected by the first objective lens OB1 of the first optical head 51, enters the optical fiber F12, and is propagated in the optical fiber F12. The fluorescence OF1 enters the first wavelength multiplexer/demultiplexer 65, is collimated by the lens L1, and then reaches the band pass filter B1.

In general, the wavelength of fluorescence generated by irradiation with excitation light is longer than the wavelength of excitation light. That is, if the central wavelength of excitation light is represented by $\lambda e$ and the central wavelength of fluorescence is represented by $\lambda f$, $\lambda e < \lambda f$ is satisfied. Therefore, in order to guide only the fluorescence OF1 to the first fluorescence detector 66, as the band pass filter B1, one having a spectral characteristic of reflecting light having a wavelength of $\lambda e$ and transmitting light having a wavelength of $\lambda f$ is used. The band pass filter B1 is designed so as to transmit light having a wavelength in a range not overlapping with the wavelength of the excitation light OE1 in the fluorescence OF1. The fluorescence OF1 that has passed through the band pass filter B1 is collected by a lens L2 and enters an optical fiber F13. The band pass filter B1 has a function of reflecting excitation light and transmitting fluorescence. Therefore, an edge filter that can reflect light in a wavelength range including $\lambda e$ and transmit light in a wavelength range including $\lambda f$ according to central wavelengths thereof can be used instead of the band pass filter.

The fluorescence OF1 that has been propagated in the optical fiber F13 reaches the first fluorescence detector 66. The fluorescence OF1 may pass through the band pass filter Cl before entering the first fluorescence detector 66 in order to precisely adjust the wavelength range. Only light having a wavelength in a predetermined range with a central wavelength of about 530 nm, which has passed through the band pass filters B1 and Cl, enters the first fluorescence detector 66. The first fluorescence detector 66 is, for example, a photoelectric conversion element such as PD, APD, or a photomultiplier. A signal that has been converted into an electrical signal by the first fluorescence detector 66 is subjected to signal processing described later.

In the first fluorescence detection device 50 illustrated in FIG. 3, each element may include a lens for efficiently transmitting or combining light or improving utilization efficiency of a band pass filter. Examples of the lens include a graded refractive index lens, a ball lens, and an aspheric lens. In the first fluorescence detection device 50 illustrated in FIG. 3, the optical fibers F11, F12, and F13 can be single mode fibers or multimode fibers.

The first fluorescence detection device 50 having the above configuration irradiates a sample with light having a central wavelength of 470 nm and a wavelength range of about 450 to 490 nm as the first excitation light OE1, and detects the first fluorescence OF1 having a central wavelength of 530 nm and a wavelength range of about 510 to 550 nm, emitted from the sample. Those skilled in the art can understand that characteristics related to a wavelength are determined by a combination of transmission or reflection characteristics of each band pass filter as described above, and that a change thereof and customization thereof are also possible.

Meanwhile, in the present embodiment, the second fluorescence detection device 54 can detect fluorescence from a sample containing ROX as a fluorescent dye. The second fluorescence detection device 54 irradiates a sample with light having a central wavelength of 530 nm and a wavelength range of about 510 to 550 nm as the second excitation light OE2, and detects the second fluorescence OF2 having a central wavelength of 610 nm and a wavelength range of about 580 to 640 nm.

Figure 4:
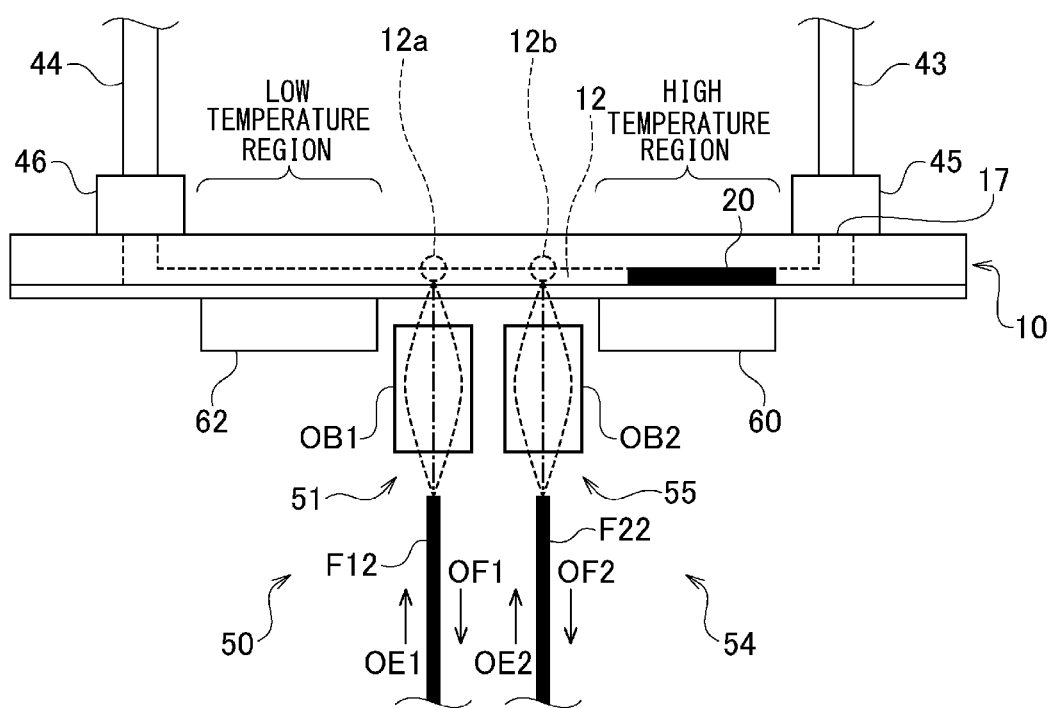
FIG. 4 is a diagram illustrating a state in which a first optical head of a first fluorescence detection device and a second optical head of a second fluorescence detection device are disposed.

FIG. 4 illustrates a state in which the first optical head 51 of the first fluorescence detection device 50 and the second optical head 55 of the second fluorescence detection device 54 are disposed. The first optical head 51 is disposed so as to be able to detect fluorescence from the sample 20 passing through the first fluorescence detection region 12a of the channel 12. The second optical head 55 is disposed so as to be able to detect fluorescence from the sample 20 passing through the second fluorescence detection region 12b of the channel 12. The first optical head 51 and the second optical head 55 are held by a holding member (not illustrated in FIG. 4, refer to FIG. 5).

As illustrated in FIG. 4, the first optical head 51 collects the first excitation light OE1 that has been propagated in the optical fiber F12 with the first objective lens OB1 to irradiate the sample 20 passing through the first fluorescence detection region 12a with the collected light, and collects the first fluorescence OF1 generated from the sample 20 with the first objective lens OB1 to cause the collected light to enter the optical fiber F12. Similarly, the second optical head 55 collects the second excitation light OE2 that has been propagated in the optical fiber F22 with the second objective lens OB2 to irradiate the sample 20 passing through the second fluorescence detection region 12b with the collected light, and collects the second fluorescence OF2 generated from the sample 20 with the second objective lens OB2 to cause the collected light to enter the optical fiber F22.

As the first objective lens OB1 and the second objective lens OB2, it is possible to use a lens or a lens group having a positive power, for example, a SELFOC (registered trademark) microlens which is a graded refractive index lens. As the first objective lens OB1 and the second objective lens OB2, for example, those having a diameter of 1.8 mm, a numerical aperture (NA) of 0.23, and a working distance (WD) of 1 mm to 3 mm can be used.

In the present embodiment, a first excitation light source of the first fluorescence detection device 50 is modulated by a first modulation signal and emits light in a blinking manner. Similarly, a second excitation light source of the second fluorescence detection device 54 is modulated by a second modulation signal and emits light in a blinking manner.

In the present embodiment, the first optical head 51 and the second optical head 55 are disposed side by side in a longitudinal direction of the channel 12 in order to detect the sample 20 passing through the single channel 12. As described above, the first fluorescence detection device 50 emits the first excitation light OE1 having a central wavelength of 470 nm and a wavelength range of about 450 to 490 nm, and detects the first fluorescence OF1 having a central wavelength of 530 nm and a wavelength range of about 510 to 550 nm. The second fluorescence detection device 54 emits the second excitation light OE2 having a central wavelength of 530 nm and a wavelength range of about 510 to 550 nm, and detects the second fluorescence OF2 having a central wavelength of 610 nm and a wavelength range of about 580 to 640 nm. Therefore, the wavelength range (about 510 to 550 nm) of the second excitation light OE2 and the wavelength range (about 510 to 550 nm) of the first fluorescence OF1 overlap with each other. In this case, when a part of the second excitation light OE2 emitted from the second optical head 55 may be detected by the first optical head 51, there is a possibility that the second excitation light OE2 is not removed by the band pass filters B1 and C1 in a later stage of the first optical head 51 and reaches the first fluorescence detector 66. The second excitation light OE2 is a noise in the first fluorescence detector 66, and there is a possibility that the first fluorescence OF1 to be originally detected cannot be detected.

Such a problem does not occur when the first optical head 51 and the second optical head 55 are disposed sufficiently apart from each other. However, in this case, the size of the reaction processor 30 is increased. In order to solve such contradictory problems, the present inventor analyzed a phenomenon that, when two optical heads are disposed side by side, excitation light emitted from one optical head reaches the other optical head as a noise by optical simulation.

Figure 5:
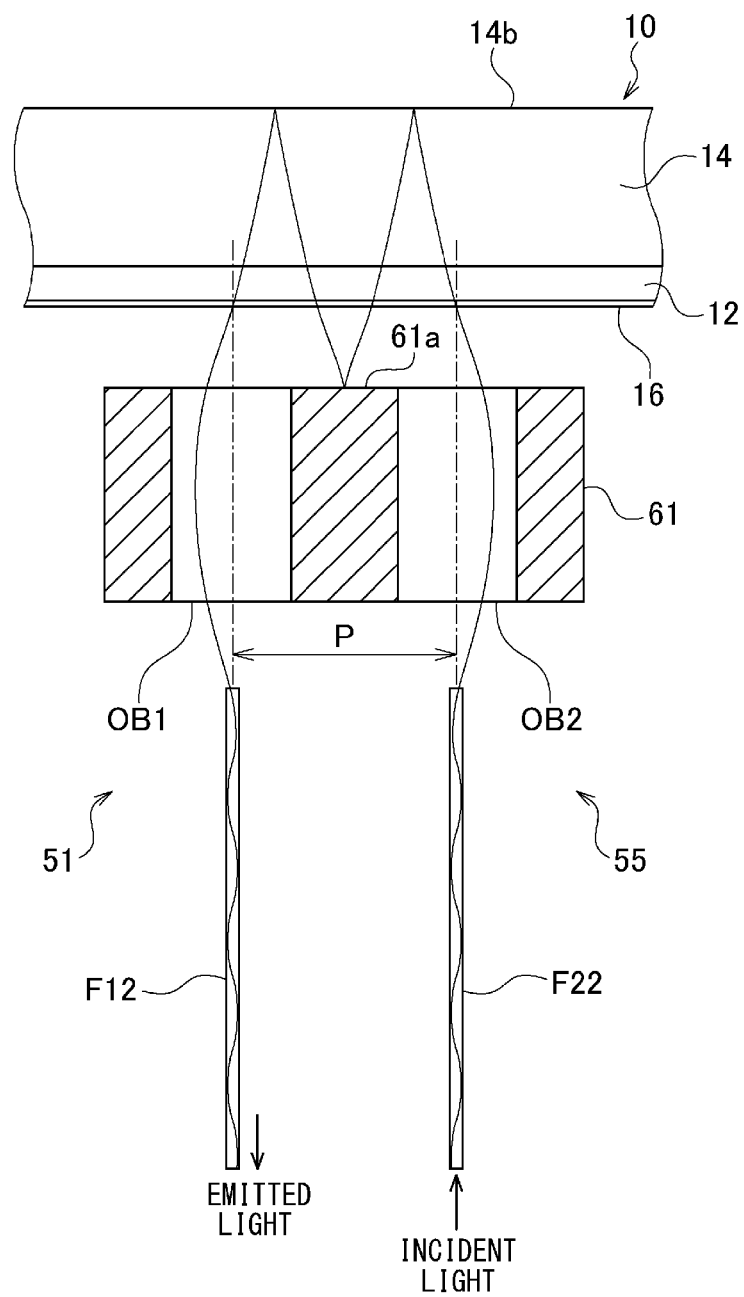
FIG. 5 is a diagram illustrating a model of optical simulation.

FIG. 5 is a diagram illustrating a model of optical simulation. In this optical simulation, the first objective lens OB1 and the second objective lens OB2 were graded refractive index type lenses each having a diameter of 1.8 mm, a central refractive index of 1.616 (wavelength=530 nm), $\sqrt{A}$ (optical constant) of 0.346 mm$^{-1}$ (wavelength=530 nm), and a lens length of 4.45 mm. The optical fibers F12 and F22 were multimode fibers each having a core diameter of 200 μm, a cladding diameter of 220 μm, and NA of 0.3. A working distance between the objective lens and the multimode fiber was 1.8 mm.

As illustrated in FIG. 5, the first objective lens OB1 and the second objective lens OB2 were held by a stainless steel holding member 61. A distance between the optical axis of the first objective lens OB1 and the optical axis of the second objective lens OB2 is referred to as "center-to-center distance P". Side surfaces of the first objective lens OB1 and the second objective lens OB2 were fixed to the holding member 61 via an epoxy adhesive layer having a thickness of 10 μm. An upper surface 61a of the holding member 61 is flush with excitation light emitting side end surfaces of the first objective lens OB1 and the second objective lens OB2.

As for the reaction processing vessel 10, a cycloolefin polymer substrate (refractive index 1.53) having a thickness of 4 mm was used as the substrate 14. The channel 12 having a width of 0.7 mm, a depth of 0.7 mm, and a square cross section was formed on a lower surface of the substrate 14, and a lower surface of the channel 12 was sealed by the channel sealing film 16 (made of cycloolefin polymer, refractive index 1.53) having a thickness of 0.1 mm. This optical simulation adopted a model in which a substance having a refractive index of 1 (corresponding to air) is present in the channel 12 if the channel is empty, and a substance having a refractive index of 1.333 (corresponding to water) is present if a sample is present in the channel.

A distance between an objective lens and a sample was based on a working distance of 1.8 mm (matched with a working distance between the objective lens and a multimode fiber) as an equal magnification imaging system such that a lower surface of the channel 12 (an upper surface of the channel sealing film 16) was an image forming position by correcting (moving away) the image forming position by a deviation of the image forming position due to presence of the channel sealing film 16 in an optical path.

Optical simulation was performed for a case where light was caused to enter an end surface of the optical fiber F22 opposite to the second objective lens OB2 and the light was emitted from the second objective lens OB2 by constituting the model as described above. Results of the optical simulation are illustrated in FIG. 5.

As illustrated in FIG. 5, a light beam (corresponding to excitation light) emitted from the second objective lens OB2 of the second optical head 55 passed through the channel 12 and was reflected by the second main surface 14b of the substrate 14, and the reflected light passed through the channel 12 in the opposite direction. Thereafter, the light beam was reflected by the upper surface 61a of the holding member 61 between the two objective lenses, passed through the channel 12 again, and was reflected by the second main surface 14b of the substrate 14. The reflected light passed through the channel 12 again in the opposite direction, was received by the first objective lens OB1 of the first optical head 51, and was emitted through the optical fiber F12. From this optical simulation, it has been found that excitation light emitted from one optical head reaches the other optical head as a noise due to such an optical path.

Figure 6:
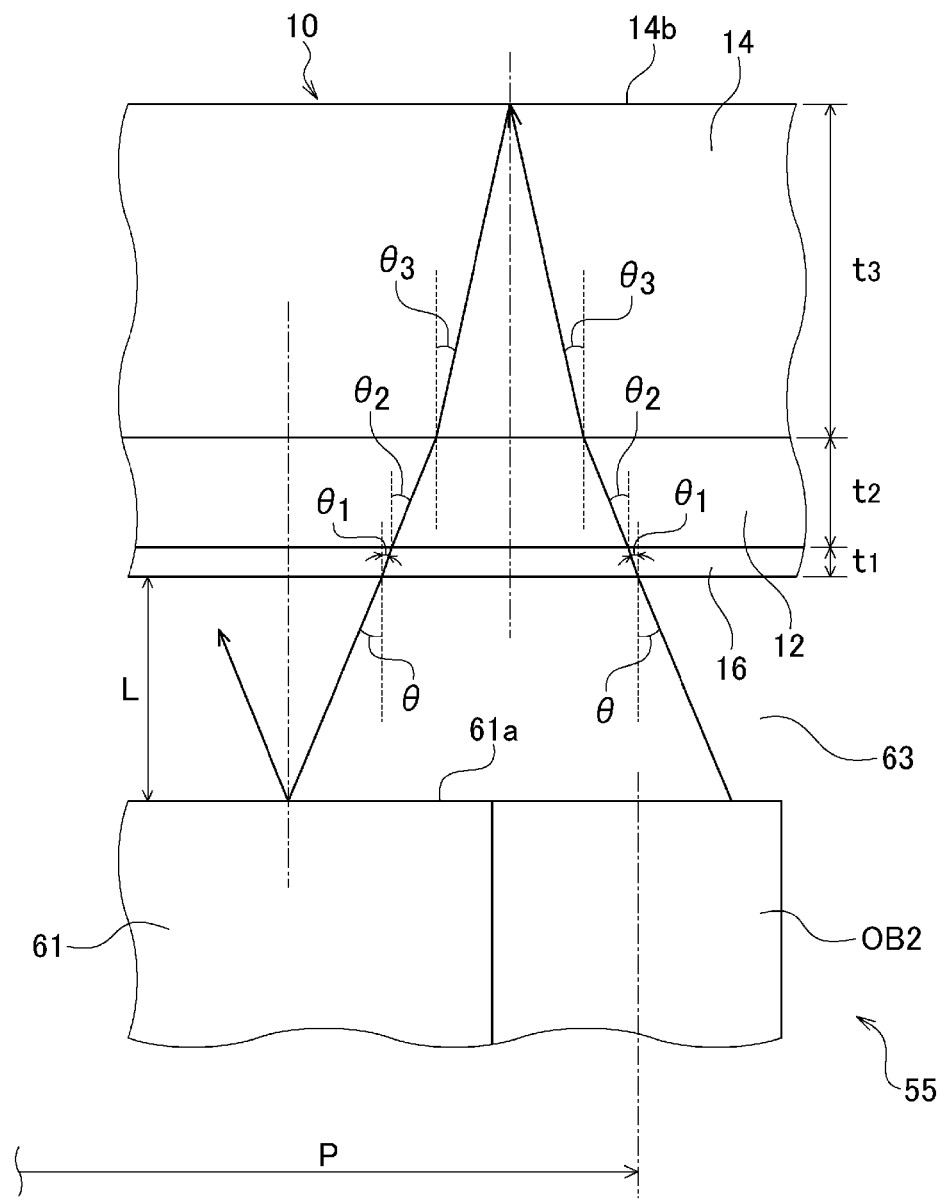
FIG. 6 is a diagram for explaining derivation of a center-to-center distance between two optical heads.

FIG. 6 is a diagram for explaining derivation of the center-to-center distance P between two optical heads. As described in FIG. 5, regarding a light beam emitted from the second objective lens OB2 of the second optical head 55 and received by the first objective lens OB1 of the first optical head 51, the following formula (1) is satisfied by applying Snell's law to each interface if an angle formed by a light beam emitted from the second objective lens OB2 with the optical axis of the second objective lens OB2 (incident angle with respect to the channel sealing film 16) is represented by θ, a refraction angle at an interface between an air layer 63 between the second objective lens OB2 and the channel sealing film 16 and the channel sealing film 16 is represented by $θ_1$, a refraction angle at an interface between the channel sealing film 16 and the channel 12 is represented by $θ_2$, a refraction angle at an interface between the channel 12 and the substrate 14 is represented by $θ_3$, the refractive index of the channel sealing film 16 is represented by $n_1$, the refractive index of the channel 12 is represented by $n_2$ (varies depending on whether a sample is present or absent (that is, in a case of air) in the channel 12), and the refractive index of the substrate 14 is represented by $n_3$.

$$\sin θ = n_1 \cdot \sin θ_1 = n_2 \cdot \sin θ_2 = n_3 \cdot \sin θ_3 \quad (1)$$

In consideration of geometrical symmetry, the center-to-center distance P between the two optical heads can be expressed as the following formula (2) as the sum of channel longitudinal components of an optical path.

$$P = (L \cdot \tan θ + t_1 \cdot \tan θ_1 + 2 \cdot t_2 \cdot \tan θ_2 + 2 \cdot t_3 \cdot \tan θ_3) \times 2 = 2 \cdot L \cdot \tan θ + 2 \cdot t_1 \cdot \tan θ_1 + 4 \cdot t_2 \cdot \tan θ_2 + 4 \cdot t_3 \cdot \tan θ_3 \quad (2)$$

In formula (2), L represents a distance (mm) from the upper surface 61a of the holding member 61 to the channel sealing film 16, $t_1$ represents the thickness (mm) of the channel sealing film 16, $t_2$ represents the depth (mm) of the channel 12, and $t_3$ represents a thickness (mm) from a bottom of the channel 12 to the second main surface 14b of the substrate 14.

The relationship of the following formula (3) is satisfied between sine and tape.

$$1/\tan^2 θ + 1 = 1/\sin^2 θ \quad (3)$$

When formula (3) is transformed, the following formula (4) is obtained.

$$\tan θ = \sin θ / \sqrt{(1-\sin^2 θ)} \quad (4)$$

If the relationship of formula (4) is applied to formula (2), the following formula (5) is obtained.

$$P = 2 \cdot L \cdot \sin θ / \sqrt{(1-\sin^2 θ)} + 2 \cdot t_1 \cdot \sin θ_1 / \sqrt{(1-\sin^2 θ_1)} + 4 \cdot t_2 \cdot \sin θ_2 / \sqrt{(1-\sin^2 θ_2)} + 4 \cdot t_3 \cdot \sin θ_3 / \sqrt{(1-\sin^2 θ_3)} \quad (5)$$

When formula (1) is put into formula (5), the following formula (6) is obtained.

$$P = 2 \cdot L \cdot \sin θ / (1-\sin^2 θ) + 2 \cdot t_1 \cdot \sin θ / \sqrt{(n_1^2 - \sin^2 θ)} + 4 \cdot t_2 \cdot \sin θ / \sqrt{(n_2^2 - \sin^2 θ)} + 4 \cdot t_3 \cdot \sin θ / \sqrt{(n_3^2 - \sin^2 θ)} \quad (6)$$

In formula (6), the third term on the right side is large when $n_2$ is small (that is, when a sample is absent in the channel 12 and air is present therein), and the center-to-center distance P is a maximum value $P_{max}$ when θ is a maximum value $θ_{max}$ (opening angle), that is, when θ is an angle corresponding to NA of an objective lens of an optical head.

From the above, if the numerical aperture corresponding to $θ_{max}$ is represented by NA, $P_{max}$ can be expressed by the following formula (7).

$$P_{max} = 2 \cdot P_0 + 2 \cdot P_1 + 4 \cdot P_2 + 4 \cdot P_3 \quad (7)$$

Here, $P_0 = L \cdot NA / \sqrt{(1-NA^2)}$ $P_1 = t_1 \cdot NA / \sqrt{(n_1^2 - NA^2)}$ $P_2 = t_2 \cdot NA / \sqrt{(1-NA^2)}$ $P_3 = t_3 \cdot NA / \sqrt{(n_3^2 - NA^2)}$ If the center-to-center distance P between the two optical heads is larger than $P_{max}$ expressed by formula (7), it is possible to avoid arrival of excitation light emitted from one optical head (second optical head 55) at the other optical head (first optical head 51). That is, in the reaction processor 30 according to the present embodiment, the center-to-center distance P satisfies the following formula (8).

$$P_{max} = 2 \cdot P_0 + 2 \cdot P_1 + 4 \cdot P_2 + 4 \cdot P_3 < P \quad (8)$$

By disposing the optical heads such that the center-to-center distance P satisfies formula (8), it is possible to avoid arrival of excitation light emitted from one optical head at the other optical head, and therefore interference among fluorescence detection devices can be suppressed. As a result, a stable fluorescence signal can be obtained, and a reaction processor having good measurement accuracy can be achieved.

Here, $1.1 \times P_{max} \leq P$ (that is, safety factor is 1.1) is preferably satisfied, and $1.2 \times P_{max} \leq P$ (that is, safety factor is 1.2) is more preferably satisfied in consideration of errors of parameters and the like.

Although the lower limit of the center-to-center distance P has been described above, the upper limit of the center-to-center distance P can be determined according to a length S (mm) of a linear portion of the channel 12 in which the two optical heads are disposed. The length S of the linear portion of the channel 12 is the length of the connecting region in the channel 12 (see FIG. 1A). Each of the first optical head 51 and the second optical head 55 is preferably disposed such that the optical axis thereof is positioned inward from an end of the linear portion of the channel 12 by a predetermined length ΔS (mm). That is, the two optical heads are preferably disposed such that the center-to-center distance P satisfies $P \leq S - 2 \times ΔS$. For example, ΔS may be 1 mm. By disposing the optical heads in this manner, fluorescence can be detected stably.

In the above embodiment, the channel 12 has a square cross section. However, the cross sectional shape of the channel 12 may be, for example, a rectangle, a trapezoid, a semicircle, or any other shape. By using a point intersecting with the optical axis of an optical head as a bottom of the channel 12, the channel 12 can be treated in a similar manner to the above.

In the above embodiment, a light absorbing layer for absorbing excitation light may be disposed between the bottom of the channel 12 and the second main surface 14b in the substrate 14. As illustrated in FIG. 5, the excitation light reaching one optical head (first optical head 51) as noise light from the other optical head (second optical head 55) passes through an area between the bottom of the channel 12 and the second main surface 14b in the substrate 14 four times. Therefore, by disposing the light absorbing layer between the bottom of the channel 12 and the second main surface 14b in the substrate 14, noise light reaching one optical head from the other optical head can be attenuated. Therefore, interference among fluorescence detection devices can be suppressed more reliably.

Next, Examples of the present invention will be described.

Example 1

Figure 7:
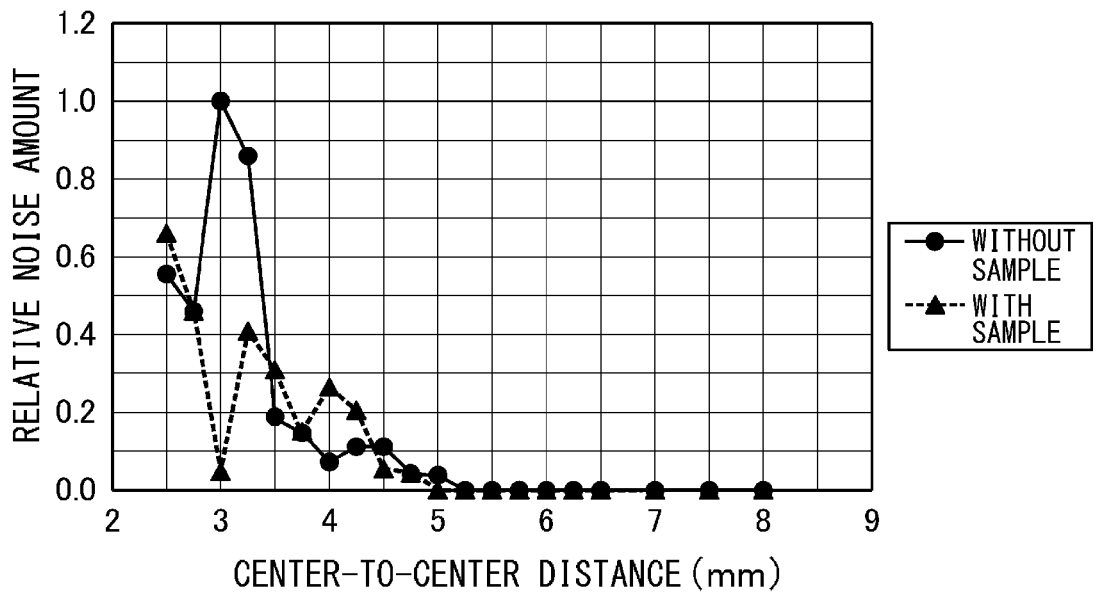
FIG. 7 is a graph illustrating a change in relative noise amount when a center-to-center distance between two optical heads is changed in Example 1 of the present invention.

In Example 1, in the configuration illustrated in FIG. 5, in order to emphasize and evaluate reflected light, the upper surface 61a of the holding member 61 between the two objective lenses was used as a mirror surface (surface where light that has reached the upper surface 61a is reflected according to Snell's law), and 25000 light beams (wavelength 530 nm) were emitted from the vicinity of an end surface of the optical fiber F22 of the second optical head 55 toward the optical fiber F22 under conditions of a diameter of 200 μm (corresponding to the core diameter of a multimode fiber) and Lambertian of 17.5° (corresponding to NA (0.3) of a multimode fiber). The intensity of a light beam reaching an evaluation surface disposed in the vicinity of the end surface of the optical fiber F12 of the first optical head 51 was determined by optical simulation. FIG. 7 illustrates a change in relative intensity of light beams when the center-to-center distance P between the two optical heads was changed in a range of 2.5 mm to 8.0 mm.

By putting parameters of L=1.735 mm, NA=0.3, $t_1$=0.1 mm, $t_2$=0.7 mm, $t_3$=3.3 mm, $n_1$=1.53, and $n_3$=1.53 into the above formula (7), $P_{max}$=4.65 mm is obtained. In the above, it has been described that by setting $P_{max}$<P, it is possible to prevent excitation light from one optical head from reaching the other optical head. From the simulation result illustrated in FIG. 7, it has been confirmed that a noise can be suppressed to a sufficiently small value (relative noise amount is about 0.1 or less) when $P_{max}$=4.65 mm<P is satisfied. In addition, it has been confirmed that a noise can be suppressed to a smaller value (relative noise amount is less than about 0.1) when 1.1× $P_{max}$=5.12 mm≤P is satisfied and that generation of a noise can be reliably suppressed (relative noise amount is less than 0.05) when 1.2× $P_{max}$=5.58 mm≤P is satisfied.

In Example 1, as the objective lens, a graded index type lens capable of effectively taking in light emitted from a multimode fiber of NA=0.3 was used, and such a configuration that working distances of the objective lens on the incident side and the emission side were equal (equal magnification imaging system) was used. Therefore, NA corresponding to an opening angle which is an angle at which an incident light beam is viewed from a focal position on the optical axis without the channel sealing film 16 can be regarded as being substantially equal to NA of light emitted from a multimode fiber.

Example 2

Figure 8:
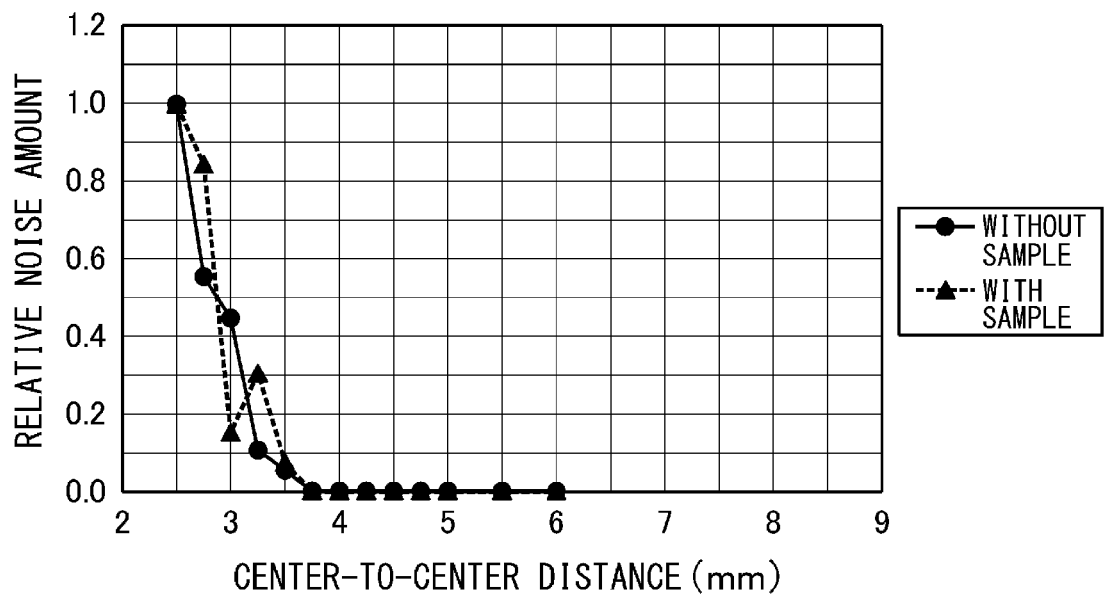
FIG. 8 is a graph illustrating a change in relative noise amount when a center-to-center distance between two optical heads is changed in Example 2 of the present invention.

In Example 2, a pinhole with a diameter of 0.8 mm was disposed on an emission end surface of the second objective lens OB2 of the second optical head 55. The other conditions were similar to those in Example 1, and the intensity of a light beam reaching an evaluation surface was determined by optical simulation. FIG. 8 illustrates a change in relative intensity of a light beam when the center-to-center distance P between the two optical heads was changed in a range of 2.5 mm to 6.0 mm.

NA in Example 2 is determined by NA=sin θ=sin(tan$^{-1}$ (0.4/1.8))=0.22 as a sine of an angle at which an aperture of a pinhole is viewed from a focal position on the optical axis without the channel sealing film 16. By putting parameters of L=1.735 mm, NA=0.22, $t_1$=0.1 mm, $t_2$=0.7 mm, $t_3$=3.3 mm, $n_1$=1.53, and $n_3$=1.53 into the above formula (7), $P_{max}$=3.36 mm is obtained. From the simulation result illustrated in FIG. 8, it has been confirmed that a noise can be suppressed to a sufficiently small value (relative noise amount is about 0.1 or less) when $P_{max}$=3.36 mm<P is satisfied. In addition, it has been confirmed that a noise can be suppressed to a smaller value (relative noise amount is less than about 0.1) when 1.1×$P_{max}$=3.70 mm≤P is satisfied and that generation of a noise can be reliably suppressed (relative noise amount is less than 0.05) when 1.2× $P_{max}$=4.03 mm≤P is satisfied.

Next, another embodiment of the present invention will be described. In the above embodiment, in a case where two optical heads in which the excitation light wavelength and the fluorescence wavelength overlap with each other are disposed side by side, by using a configuration in which the center-to-center distance P between the two optical heads satisfies formula (8), arrival of excitation light emitted from one optical head at the other optical head is suppressed. However, from the results of optical simulation illustrated in FIGS. 7 and 8, if the intensity of noise light can be reduced by one digit (that is, reduced to 10%) by the light absorbing layer disposed on the substrate 14, it can be expected to reduce the noise amount to an acceptable level even when the center-to-center distance P between the two optical heads is equal to or less than $P_{max}$ expressed by formula (7).

In general, if the intensity of incident light is represented by $I_0$ and the intensity of emitted light is represented by I, the absorbance of a substance can be represented by −ln (I/$I_0$). In order to cause light to pass through the light absorbing layer of the substrate 14 four times to make noise light 10%, it is only required to set the absorbance of the light absorbing layer to −¼·ln (0.1)≈0.58. Therefore, if an absorbance A of the light absorbing layer of the substrate 14 satisfies A≥0.58, the intensity of noise light reaching one optical head from the other optical head can be reduced to 10% or less. An actual light beam enters the light absorbing layer of the substrate 14 at an angle of $θ_3$ as illustrated in FIG. 6. If the thickness of the light absorbing layer is represented by $t_3$', an optical path length is $t_3$'/cos $θ_3$ when light passes through the light absorbing layer once. However, it is only required to dispose the light absorbing layer such that an absorption coefficient α≥0.58/$t_3$' is satisfied at the thickness $t_3$' by treating the minimum value $t_3$' as the optical path length with a margin. By disposing such a light absorbing layer on the substrate 14, noise light reaching one optical head from the other optical head can be reduced. Therefore, interference among the fluorescence detection devices can be suppressed.

Although the light absorbing layer for reducing noise light to 10% has been described above, it is more preferable to be able to reduce noise light to 5%, and it is still more preferable to be able to reduce noise light to 1%. In order to reduce noise light to about 5%, it is only required to dispose the light absorbing layer such that an absorption coefficient α≥−¼·ln (0.05)/$t_3$'≈0.75/$t_3$' is satisfied for a target wavelength. In order to reduce noise light to about 1%, it is only required to dispose the light absorbing layer such that an absorption coefficient α≥−¼·ln (0.01)/$t_3$'≈1.15/$t_3$' is satisfied for a target wavelength.

The light absorbing layer may be disposed on the entire area between the bottom of the channel 12 and the second main surface 14b in the substrate 14 or may be disposed on a part of the substrate 14 in a thickness direction thereof by forming the substrate 14 itself with a light absorbing material. Alternatively, the light absorbing layer may be separately disposed on the second main surface 14b of the substrate 14 in a state having a refractive index matched with that of the substrate 14. Here, "a state having a refractive index matched with that of the substrate 14" means that a difference between a refractive index in front of an interface and a refractive index behind the interface is 0.025 or less.

Hereinafter, Examples will be described regarding the other embodiment of the present invention described above.

Example 3

Example 3 is an example in which a light absorbing layer is disposed on the entire area between the bottom of the channel 12 and the second main surface 14b in the substrate 14. In Example 3, as in Example 1, L=1.735 mm, NA=0.3, $t_1$=0.1 mm, $t_2$=0.7 mm, $t_3$=3.3 mm, $n_1$=1.53, and $n_3$=1.53 were used. In Example 3, the center-to-center distance P was 3.5 mm, which is smaller than $P_{max}$=4.65 mm obtained in Example 1. The light absorbing layer having a thickness of $t_3'$=3.3 mm and an absorption coefficient α of 0.58/0.33=1.76 cm$^{-1}$ was disposed between the bottom of the channel 12 and the second main surface 14b in the substrate 14, and the intensity of a light beam reaching an evaluation surface was determined by optical simulation as in Example 1.

As a result of the optical simulation, in Example 3, the relative noise amount was 0.02 in a case where a sample was not present in the channel 12, and the relative noise amount was 0.03 in a case where a sample was present in the channel 12. From FIG. 7, in Example 1, when the center-to-center distance P was 3.5 mm, the relative noise amount was 0.19 in a case where a sample was not present in the channel 12, and the relative noise amount was 0.31 in a case where a sample was present in the channel 12. Therefore, it was confirmed that Example 3 in which the light absorbing layer was disposed on the substrate 14 could reduce the noise amount to about 10% as compared with Example 1.

Example 4

Example 4 is an example in which a light absorbing layer is disposed on the second main surface 14b of the substrate 14. In Example 4, as in Example 2, a pinhole with a diameter of 0.8 mm was disposed on an emission end surface of the second objective lens OB2 of the second optical head 55. In Example 4, the center-to-center distance P was 2.75 mm, which is smaller than $P_{max}$=3.36 mm obtained in Example 2. In Example 4, the light absorbing layer having a refractive index of 1.53, a thickness of 1.0 mm, and an absorption coefficient α of 0.58/0.1=5.8 cm$^{-1}$ was disposed via a resin layer having a refractive index of 1.53 and a thickness of 0.1 mm without substantial absorption on the second main surface 14b of the substrate 14, and the intensity of a light beam reaching an evaluation surface was determined by optical simulation as in the above Examples under a condition that a sample was present in the channel 12.

As a result of the optical simulation, in Example 4, the relative noise amount was 0.1. From FIG. 8, in Example 2, when the center-to-center distance P was 2.75 mm, the relative noise amount was 0.85 in a case where a sample was present in the channel 12. Therefore, it was confirmed that Example 4 in which the light absorbing layer was disposed on the second main surface 14b of the substrate 14 could reduce the noise amount to about 12% as compared with Example 2.

Example 5

In Example 5, only the absorption coefficient of a light absorbing layer disposed on the second main surface 14b of the substrate 14 was changed from Example 4. In Example 5, an absorption coefficient α of the light absorbing layer was set to α=0.75/0.1=7.5 cm$^{-1}$, and the intensity of a light beam reaching an evaluation surface was determined by optical simulation as in the above Examples.

As a result of the optical simulation, in Example 5, the relative noise amount was 0.05. As compared with the relative noise amount (0.85) in Example 2 (center-to-center distance P=2.75 mm), it was confirmed that Example 5 could reduce the noise amount to about 6%.

In Example 5 in which the absorption coefficient α of the light absorbing layer was 7.5 cm$^{-1}$, when optical simulation was performed similarly by changing the refractive index of the resin layer disposed between the substrate 14 and the light absorbing layer within a range of 1.530 to 1.505 (difference in refractive index: 0.025), the maximum intensity of a light beam reaching an evaluation surface stopped at an increase of about 2% as compared with the case where the refractive index of the resin layer was 1.530.

Example 6

Also in Example 6, only the absorption coefficient of a light absorbing layer disposed on the second main surface 14b of the substrate 14 was changed from Example 4. In Example 6, an absorption coefficient α of the light absorbing layer was set to α=1.15/0.1=11.5 cm$^{-1}$, and the intensity of a light beam reaching an evaluation surface was determined by optical simulation as in the above Examples.

As a result of the optical simulation, in Example 6, the relative noise amount was 0.01. As compared with the relative noise amount (0.85) in Example 2 (center-to-center distance P=2.75 mm), it was confirmed that Example 6 could reduce the noise amount to about 1%.

Hitherto, the present invention has been described based on the embodiments. These embodiments are intended to be illustrative only, and it will be obvious to those skilled in the art that various modifications to constituting elements and processes could be developed and that such modifications are also within the scope of the present invention.

INDUSTRIAL APPLICABILITY

The present invention is applicable to a polymerase chain reaction (PCR).

What is claimed is:
1. A reaction processor comprising:
   a reaction processing vessel including a substrate having a first main surface with a channel through which a sample moves, and a channel sealing film disposed on the first main surface so as to seal the channel;
   a first optical head including a first objective lens structured to irradiate a sample in the channel with first excitation light and to collect first fluorescence generated from the sample by irradiation with the first excitation light;
   a second optical head including a second objective lens structured to irradiate a sample in the channel with second excitation light and to collect second fluorescence generated from the sample by irradiation with the second excitation light; and
   a holding member holding the first optical head and the second optical head, wherein
   the first optical head and the second optical head are disposed side by side in a longitudinal direction of the channel,
   a wavelength range of the first fluorescence and a wavelength range of the second excitation light at least partially overlap with each other, and
   the holding member has a surface that faces the channel sealing film,
   the surface of the holding member that faces the channel sealing film is flush with excitation light emitting side end surfaces of the first objective lens and the second objective lens, a distance P between an optical axis of the first objective lens and an optical axis of the second objective lens satisfies the following formula:

$2 \cdot P_0 + 2 \cdot P_1 + 4 \cdot P_2 + 4 \cdot P_3 < P$, $P_0 = L \cdot NA / \sqrt{(1-NA^2)}$, $P_1 = t_1 \cdot NA / \sqrt{(n_1^2 - NA^2)}$, $P_2 = t_2 \cdot NA / \sqrt{(1-NA^2)}$, and $P_3 = t_3 \cdot NA / \sqrt{(n_3^2 - NA^2)}$ (in which L represents a distance from the holding member to the channel sealing film, $t_1$ represents a thickness of the channel sealing film, $t_2$ represents a depth of the channel, $t_3$ represents a thickness from a bottom of the channel to a second main surface of the substrate, NA represents a numerical aperture of the first objective lens and the second objective lens, $n_1$ represents a refractive index of the channel sealing film, and $n_3$ represents a refractive index of the substrate).

2. The reaction processor according to claim 1, wherein the distance P further satisfies $1.1 \times (2 \cdot P_0 + 2 \cdot P_1 + 4 \cdot P_2 + 4 \cdot P_3) \leq P$, and more preferably satisfies $1.2 \times (2 \cdot P_0 + 2 \cdot P_1 + 4 \cdot P_2 + 4 \cdot P_3) \leq P$.

3. The reaction processor according to claim 1, wherein the distance P satisfies $P \leq S - 2 \times \Delta S$ (in which S represents a length of a linear portion of the channel in which the first optical head and the second optical head are disposed, and $\Delta S$ represents 1 mm).

4. The reaction processor according to claim 1, further comprising a light absorbing layer structured to absorb excitation light between the bottom of the channel and the second main surface in the substrate.

* * * * *